United States Patent [19]
Avellanet et al.

[11] Patent Number: 5,542,938
[45] Date of Patent: *Aug. 6, 1996

[54] MAGNETIC GUIDEWIRE COUPLING FOR CATHETER EXCHANGE

[75] Inventors: Ernesto Avellanet, Miami Lakes; Ernesto Hernandez, Miami, both of Fla.

[73] Assignee: Cordis Corporation, Miami Lakes, Fla.

[ * ] Notice: The term of this patent shall not extend beyond the expiration date of Pat. No. 5,269,758.

[21] Appl. No.: 440,115

[22] Filed: May 12, 1995

Related U.S. Application Data

[60] Continuation of Ser. No. 133,324, Oct. 8, 1993, abandoned, which is a division of Ser. No. 920,864, Jul. 28, 1992, Pat. No. 5,269,759.

[51] Int. Cl.⁶ .................................................. A61M 25/00
[52] U.S. Cl. ........................ 604/280; 604/283; 128/772
[58] Field of Search .......................... 128/772, 656–658; 604/49, 96, 165, 264, 280, 283

[56] References Cited

U.S. PATENT DOCUMENTS

| | | |
|---|---|---|
| 2,706,979 | 4/1955 | Wallace .................................. 128/1.4 |
| 3,332,425 | 7/1967 | Luborsky et al. . |
| 4,043,309 | 7/1962 | McCarthy . |
| 4,063,561 | 12/1977 | McKenna ............................ 128/207.15 |
| 4,244,362 | 1/1981 | Anderson ............................ 128/200.26 |
| 4,593,687 | 6/1986 | Gray et al. ........................... 128/200.26 |
| 4,671,287 | 6/1987 | Fiddian-Green ........................ 128/631 |
| 4,790,809 | 12/1988 | Kuntz . |

*Primary Examiner*—Corrine M. McDermott
*Attorney, Agent, or Firm*—Gerstman, Ellis & McMillin, Ltd.

[57] ABSTRACT

Apparatus and method are disclosed for facilitating balloon catheter exchange in the vascular system of a patient. The apparatus and method concern means for holding a guidewire longitudinally fixed with respect to a guiding catheter while a balloon catheter is moved over the guidewire. Specifically, the guidewire is held longitudinally fixed with respect to the guiding catheter by way of magnetic coupling. A first magnetic element constitutes a portion of the guide wire or is attached to the guide wire to move with it. A second magnetic element is located proximate the balloon catheter but is not fixed to the balloon catheter. When the guidewire is moved within the guiding catheter to a location at which the first magnetic element reaches its point of closest approach to the second magnetic element, magnetic force holds the guidewire against movement relative to the guiding catheter even while a balloon catheter is being moved over the guidewire.

9 Claims, 2 Drawing Sheets

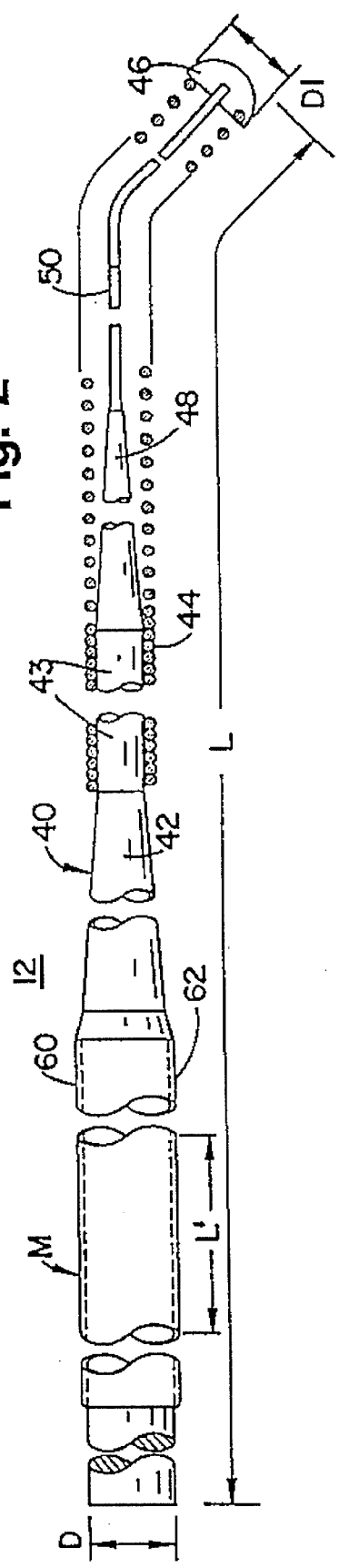
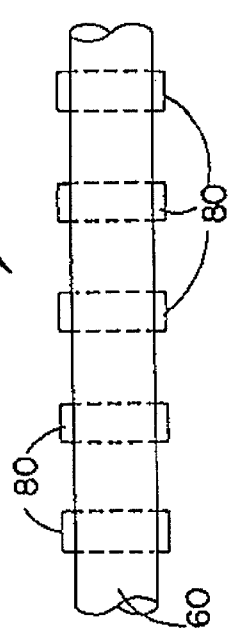
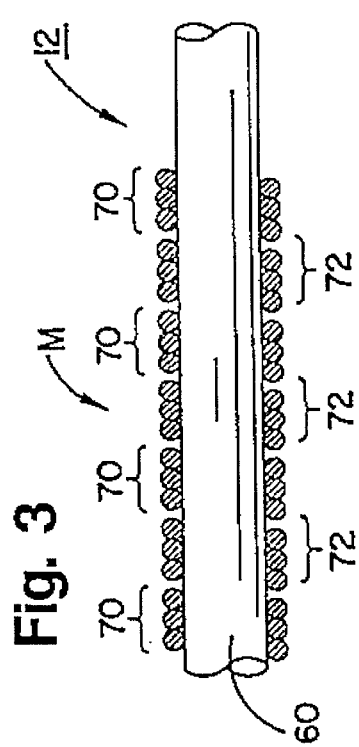
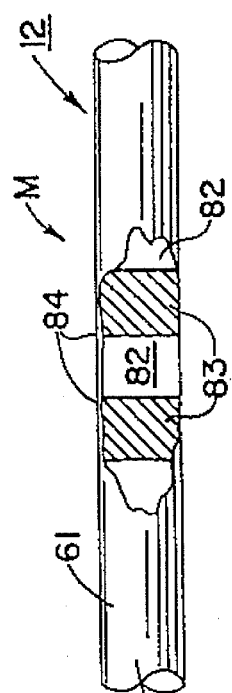
Fig. 2
Fig. 4
Fig. 5
Fig. 3

MAGNETIC GUIDEWIRE COUPLING FOR CATHETER EXCHANGE

This application is a continuation of U.S. Application Ser. No. 08/133,324 filed Oct. 8, 1993 now abandoned, which is a division of U.S. Application Ser. No. 07/920,864, filed Jul. 28, 1992, now U.S. Pat. No. 5,269,759.

BACKGROUND OF THE INVENTION

1. Technical Field

This invention relates generally to the field of catheterization, and more specifically to a novel apparatus and method for facilitating catheter exchange.

2. Background Art

Catheterization procedures are well known for diagnosis and therapy of lesions in the cardiovascular system. One such procedure is angioplasty, for eliminating or ameliorating the vascular plaque or constriction in blood vessels associated with the provision of the heart's blood supply. In an angioplasty procedure, an expandable balloon carried by an elongated catheter is introduced into the patient's arterial system and advanced until it is positioned in the region of the blockage or constriction. Once so positioned, the balloon is expanded by filling it with a liquid. In successful procedures, the expandable balloon presses outwardly against the walls of the artery and expands the artery to a degree to which the artery is either partially or totally re-opened to blood flow.

A typical angioplasty procedure for opening the coronary artery and components used in practicing the illustrative procedure, are now described.

Prior to initiating the angioplasty procedure, a guiding catheter is placed typically via the femoral artery into the aorta and its tip is engaged into the coronary arteries which branch from the aorta. This entrance into the coronary artery is called the osteum. Once placed, the guiding catheter acts as a conduit to access the coronary arteries with a guidewire and balloon catheter. The guiding catheter is a portion of plastic tubing having a length of about 95 centimeters, an inside diameter of about 0.08 inches, and an outside diameter of about 2.5 millimeters.

The physician threads a balloon catheter onto a guidewire. This operation takes place external to the patient.

The guidewire is a piece of stainless steel and platinum wire, approximately 175 centimeters in length, and about 0.010–0.018 inches in diameter. The soft distal tip of the guidewire can be shaped to form a "J" configuration. This "J" shape allows the physician to steer the wire by twisting the proximal extremity of the wire while advancing or retracting the wire.

The balloon catheter is an elongated flexible plastic member defining two longitudinal passages and having a balloon located near its distal end. One longitudinal opening defines a sleeve through which the guidewire can be passed. The other longitudinal passage defines a conduit communicating with the interior of the balloon and through which inflation fluid can be injected to inflate the balloon.

Among the types of balloon catheters is one of a type in which the two longitudinal passages are generally side by side and parallel. In another type of balloon catheter, the two longitudinal passages are co-axial. In this latter type, the balloon guidewire is passed down the inner passage and the inflation fluid is injected into the balloon via the outer passage.

Balloon catheters, as well as associated apparatus and method for use in angioplasty, are described in U.S. Pat. No. 5,040,548, issued on Aug. 20, 1991, to Yock, and U.S. Pat. No. 4,762,129, issued on Aug. 8, 1988. Each of these issued U.S. patents is hereby expressly incorporated by reference.

The physician passes the guidewire through the appropriate one of the longitudinal passages in the balloon catheter, leaving a portion of the guidewire extending from the distal end of the balloon catheter and also a portion extending from its proximal end.

This assembly is then inserted into the proximal end of the guiding catheter, distal end first. The assembly is inserted until the balloon which is attached near the distal end of the balloon catheter is near the distal end of the guiding catheter. At this point, the physician, while maintaining the balloon catheter stationary, pushes on the balloon guidewire to advance it outwardly from the distal end of the guiding catheter.

The guidewire can be steered by appropriate twisting movement by the physician.

The physician steers the guidewire into the chosen one of the coronary arteries, and advances it until it reaches a location of construction which the physician desires to re-open. Carefully, the physician eases the guidewire's distal end through the region of restriction until the guidewire tip is on the opposite side of the constriction, relative to the guiding catheter.

With the guidewire held stationary, the physician then advances the balloon catheter. The distal end of the balloon catheter, as it is advanced, will, of course, follow the balloon guidewire which is already in place.

The physician continues to advance the balloon until it is located in the region of constriction of the artery. With the balloon and its associated catheter held stationary, inflation fluid is injected into the conduit which communicates with the balloon, causing it to inflate. Inflation of the balloon expands the walls of the artery in the region of constriction and, if successful procedures, re-opens the artery to sufficient blood flow.

Arteries vary in size, and therefore balloon catheters having balloons of different sizes are provided for the physician's selection. These balloons, when inflated, range from about 1.5 millimeters to about 4 millimeters in diameter.

Sometimes, it is necessary for the physician to use more than one balloon to open an artery. Sometimes, the chosen balloon is too large to be advanced into the constricted area. In other instances, the first chosen balloon size, even when inflated, is not large enough to open the constricted area to the degree desired. In such cases, it is necessary to exchange one balloon for another during the same angioplasty procedure.

In order to accomplish this exchange, the guidewire if left in place, and the balloon catheter is withdrawn entirely from the guiding catheter until it is completely disengaged from the proximal end of the guidewire. A new balloon catheter, having a different sized balloon, is then re-inserted over the balloon guidewire and advanced back to the location of the constricted area, where it is used to effect the desired result.

Once the guidewire is initially in place, extending past the constricted area, it is highly desirable to leave the balloon guidewire in place for the entirety of the duration of the angioplasty procedure. This means that the balloon guidewire must remain in the place even during exchanges of balloons. The reason for this is that, when a foreign object, such as the balloon guidewire, is introduced into an artery, the artery walls sometimes go into spasm, and constrict generally along a substantial portion of its length. If the artery tends to contract in this way, removal of the balloon guidewire while the artery is so contracted will sometimes render it virtually impossible to re-insert the guidewire through the contracted artery.

Withdrawal of the balloon catheter, while preventing movement of the balloon guidewire, is a difficult and cumbersome procedure, requiring both a second individual, in addition to the physician, and the attachment of a removable extension of the proximal end of the guidewire.

Attachment of the extension to the guidewire during withdrawal of the balloon catheter is necessary because, if the balloon catheter were withdrawn over the proximal end of the guidewire, there would be no way that the guidewire could be manually held stationary. Attachment of the extension to the proximal end of the guidewire extends the guidewire to a point at which the proximal end of the extension still extends outwardly from the proximal end of the balloon catheter even when the balloon catheter is entirely withdrawn from the patient.

Even with the extension, the physician must enlist the aid of an assistant to manually hold stationary the end of the guidewire, preventing guidewire movement, while the physician withdraws the balloon catheter. This is a cumbersome and awkward procedure at best.

It is a general object of the present invention to provide apparatus and method for facilitating introduction and exchange of balloons in angioplasty procedures without the need for manually holding the guidewire in place.

BRIEF DESCRIPTION OF THE INVENTION

The disadvantages of the prior art are reduced or eliminated by the use of magnetic force for holding a guidewire longitudinally stationary with respect to a catheter without the use of the guidewire extension as described above.

The invention is adapted for use with catheterization apparatus including a guidewire and a catheter. Broadly stated, the invention includes structure for inhibiting longitudinal motion of the guidewire within the catheter by the application of magnetic force.

The structure for inhibiting guidewire/catheter relative longitudinal motion includes a first magnetic circuit element longitudinally fixed with respect to the guidewire, a second magnetic circuit element located external to the guidewire, such that, at a particular relative positioning of the guidewire, the two magnetic circuit elements apply magnetic force tending to inhibit longitudinal sliding motion of the guidewire. Thus, the invention facilitates holding the guidewire at a fixed longitudinal displacement without the need for external force, which would have in the past been applied by the use of an extension on the guidewire.

The first and second magnetic circuit elements together comprise, in once specific embodiment, both ferromagnetic and permanent magnetic material.

In another embodiment, one of the two circuit elements comprises an electromagnet.

A further specific feature involves placement of the two magnetic circuit element sat a location along the guidewire catheter combination at a point near, but outside the point of entry of the catheterization apparatus into the patient's vascular system.

According to a more specific feature, one or both of the magnetic circuit elements comprises both permanently magnetic and ferromagnetic portions of material, distributed alternately generally along the longitudinal dimension of the guidewire.

In another specific embodiment, the second magnetic circuit element can actually be located external to a guiding catheter.

In accordance with another feature, the first magnetic circuit element comprises a section of the balloon guidewire which is laminated. The boundaries between the laminated portions extend substantially perpendicular to the axis of the guidewire. The laminations comprise alternate layers of permanently magnetic and ferromagnetic material. The laminations are fastened together for mechanical integrity by welding.

Another feature involves respective dimensioning of the two magnetic circuit elements such that the first magnetic circuit element, which is longitudinally fixed relative to the balloon guidewire, extends along a substantially longer portion of the guidewire than does the second magnetic element, which is not longitudinally fixed relative to the guidewire. In this embodiment, the balloon guidewire is not substantially inhibited from longitudinal motion over the distance corresponding to the length of the first magnetic circuit element but in inhibited from movement outside this permitted excursion.

In accordance with another specific embodiment, the second magnetic circuit element comprises a magnet self positioned to direct magnetic flux lines through the region of a portion of the balloon guidewire, with the flux lines extending generally transverse to the axis of the guidewire.

In another embodiment, the balloon guidewire consists of a central core wire with finer wire wound around the periphery of the core. In this embodiment, the coil wound about the periphery consists of alternate sections of magnetized and ferromagnetic material.

In still another embodiment, a segment of the balloon guidewire carries a plurality of permanently magnetized washers separated one from another by ferromagnetic spacers.

The present invention will be understood in more detail by reference to the following specific description, and to the drawings, in which:

BRIEF DESCRIPTION OF THE DRAWINGS

FIG. 2 is an elevational view, partly in cross-section, showing a guidewire; and FIGS. 3, 4 and 5 show alternate embodiments of a magnetic circuit defining portion of the FIG. 2 guidewire.

DETAILED DESCRIPTION OF THE ILLUSTRATION EMBODIMENTS

Figure 1:
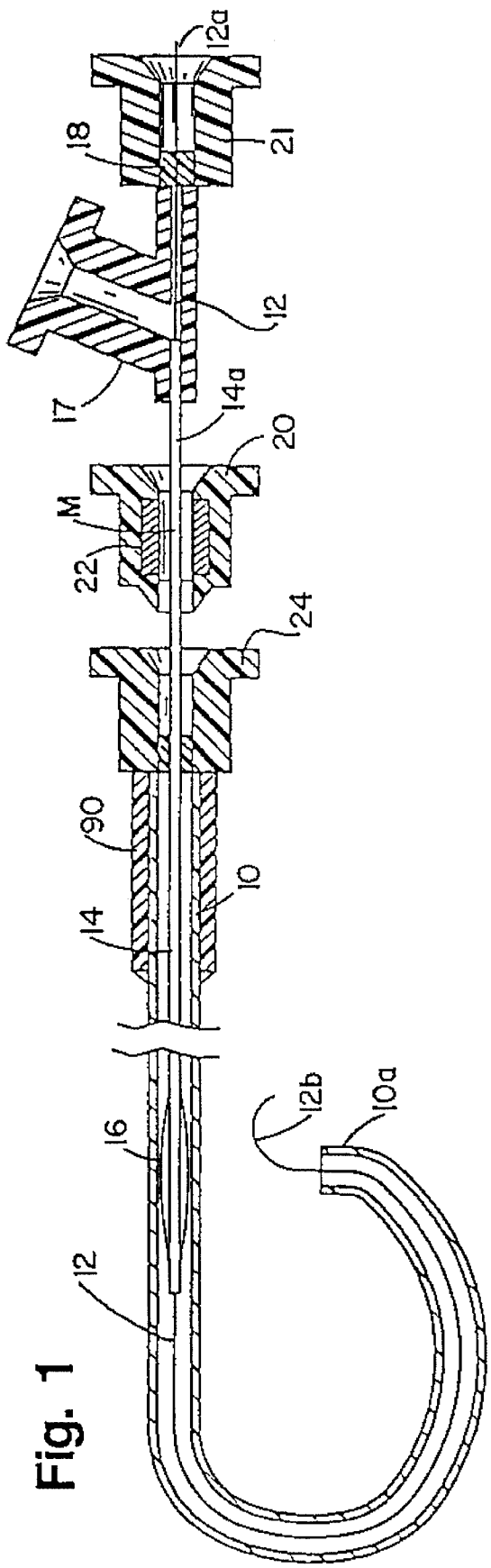
FIG. 1 is an elevational view, partly in cross-section, illustrating a guidewire, balloon catheter and guiding catheter.

One use of the present invention is to facilitate treating a subject blood vessel during an angioplasty procedure. FIG. 1 shows a guiding catheter 10 that has been positioned within the patient's arterial system as described above. A guidewire 12 is also illustrated. The guidewire extends outwardly from the proximal end of the guiding catheter 10, near the right-hand portion of FIG. 1, at reference character 12a. The guidewire 12 also extends entirely through the guiding catheter and extends outwardly from a distal end 10a of the guiding catheter with a portion indicated at reference character 12b.

A balloon catheter 14 is illustrated with the guidewire 12 passing through a longitudinal passage extending through the balloon catheter. Preferably, the balloon catheter is of the type described above wherein the longitudinal passage for accommodating the balloon guidewire is central and surrounded by a second co-axial passage for transmitting inflation fluid to a balloon 16 at the catheter's distal end.

When the balloon 16 is inflated by the injection of inflation fluid, the balloon expands in all directions to impose outward pressure on the inner walls of a blood vessel in which the balloon is located.

The balloon catheter is made of an extrusion of known relatively flexible plastic, such as nylon. The same is true of the guiding catheter.

It is to be understood that, as an alternative to the balloon catheter construction shown in FIG. 1, the balloon catheter may be of another known configuration in which the longitudinal passages extending through the balloon catheter are not co-axial. In such an alterative embodiment, the longitudinal passages through the balloon catheter are side by side and substantially parallel.

It is to be understood that, in the FIG. 1 illustration, the balloon 16 has not yet been extended from the distal end 10a of the guiding catheter 10. Rather, the balloon 16 is, in the FIG. 1 illustration, still located within the guiding catheter. The physician, however, by pushing on a proximal end 14a of the balloon catheter can advance the balloon catheter and its associated balloon 16 all the way through the guiding catheter and out of the distal end 10a of the guiding catheter 10, from which the balloon catheter and balloon will track the guidewire 12 until the balloon reaches a location of a constriction which is to be widened or re-opened.

When it is desired to inflate the balloon 16, inflation fluid is forced under pressure into an outer longitudinal passage of the balloon catheter by know means, such as a syringe. The syringe engages a side port 17 at a proximal end of the balloon catheter that defines a conventional Luer fitting. As the fluid enters the side port 17, it passes into the longitudinal passage of the catheter 14 and inflates the balloon 16. A seal 18 in a proximal catheter end fitting 21 impedes flow of the inflation fluid out the catheter's proximal end.

A plastic holding attachment 20 just proximal of the guiding catheter 10 facilitates the exchange of balloon catheters without attaching an extension to the proximal end of the guidewire 12, and without requirement for a second individual to assist the physician in effecting the catheter exchange.

The holding attachment 20 positions an annular magnet 22 to up a magnetic field in the vicinity of the proximal end of the guide catheter. The proximal end of the guide catheter 10 includes a conventional luer fitting 24 to which the attachment 20 can be connected. In a typical application, the attachment 20 is connected to a guide catheter before the balloon and guidewire are inserted into the guide catheter.

FIG. 2 is an enlarged view of the guidewire 12 having a length L from a proximal to distal end that will extend through the guide catheter 10 and extends out the proximal end of the balloon catheter a sufficient distance to allow manipulation of the guidewire. Issued U.S. Pat. No. 4,846, 186 discloses such a guidewire and is incorporated herein by reference. At the distal end of the guidewire 12, a core wire 40 has a tapered section 42. Attached to the core wire 40 at a reduced diameter portion 43 of the core wire 40, is a spring 44 which extends along the distal portion of the guidewire to a distal guidewire tip 46. A second tapered portion 48 of the core 40 causes the spring 44 to separate from the core 40 along the distal segment of the guidewire. The center or core 40 has a flattened end region 50 surrounded by the spring 44 which increases the flexibility of the distal end of the guidewire. The guidewire core 40 also includes a uniform diameter proximal segment 60 covered with a lubricous coating 62 which facilitates pushing the guidewire back and forth through the balloon catheter. A uniform diameter core section 60 has a diameter D that extends over half the distance L of the guidewire. The FIG. 2 depiction of this section 60 has been sectioned to facilitate illustration of the guidewire.

At an extreme proximal end of the guidewire, the guidewire defines a magnetic section M which is attracted to the magnet 22 carried by the holding attachment 20. FIGS. 3, 4 and 5 illustrate alternate techniques for creating the magnetic guidewire section M. In FIG. 3 embodiment, the magnetic section is constructed from alternating coil segments 70, 72 which are attached to the uniform diameter section 60 of the core wire 40. In this embodiment, the coil segments 70 are constructed of a magnetic material and the coil segments 72 are constructed from a suitable ferro magnetic material which is also attracted by the magnet 22. In an alternate embodiment shown in FIG. 4, the magnetic section M is constructed using magnetic bands 80 spaced apart along the uniform diameter section 60 of the core wire 40. The bands may be spaced apart along the magnetic section M by ferro magnetic spacer. In both FIG. 3, FIG. 4 and FIG. 5 embodiments the magnetic section is covered with the lubricous covering such a Teflon (registered trademark) coating 61.

In a further alternate embodiment shown in FIG. 5, the magnetic section M is constructed of laminations of permanently magnetic materials 82 and ferromagnetic materials 83 making up the uniform diameter section 60 of the core wire 40. The magnetic section is covered with a lubricous covering 61. The boundaries 84 between said laminations extend generally perpendicular to the axis of the guidewire.

In operation, the physician places a balloon catheter extending distally of the distal tip of the guide catheter and, under certain circumstances, determines that an exchange of catheters is necessary. When this occurs, so long as the magnetic portion M of the guidewire is in close physical proximal to the magnet 22 of the catheter holding attachment 20, the physician can grasp the proximal end of the balloon catheter and withdrawn this catheter without movement of the magnetically stabilized guidewire. Experience with the preferred embodiment of the invention indicates that a distance L for the magnetic guidewire section M is preferably 4 inches. The magnet 22 has a length dimension of approximately 1 or 2 inches.

Figure 1A:
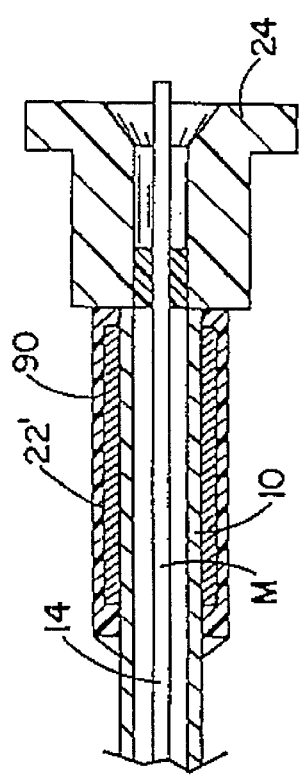
FIG. 1A is an enlarged section view of a proximal end of an alternate guiding catheter for use with the present invention.

Turning now to FIG. 1A, an alternate technique for stabilizing the position of the guidewire within the guiding catheter is illustrated. In this embodiment, a plastic sheath 90 covering the proximal end of the guide catheter supports a magnet 22 in relation to the proximally located luer fitting 24. The magnet 22 preferably has an axial length of approximately 1 inch. In this embodiment, the attachment 20 is not needed since the guide catheter provides its own magnetic attraction between guidewire and catheter. As in the above described embodiment, in the event the physician determines that exchange of the catheter 14 is required, so long as the magnetic segment M of the guidewire is in proximity of the magnet 22, the physician grasp the proximal end of the proximal end of the balloon catheter and withdraw it without accompanying movement of the guidewire 12.

The magnetic section M must be position near the proximal end but spaced slightly so that the magnet 22 and magnetic portion M are co-axial once the guidewire tip has been forced through an obstruction.

Since the magnets 22, 22 are located outside the patient, they could be electro-magnetic coupled to an external power supply. Instead of an annular magnetic, an electro-magnetic would be energized coils wound about a ferromagnetic core.

While the present invention is described above is considerable particularity, it is to be understand that those ordinary skill in the art may be able to make certain additions or modifications to, or deletions from, the specific embodiments described herein, without departing from the spirit or the scope of the invention, as set forth in the appended claims.

What is claimed is:

1. For use in catheter exchange in the vascular system of a patient in which a catheter is advanced over a guidewire member and thereafter the catheter is withdrawn over the guidewire member while the guidewire member is retained in position in the vascular system of the patient, the improvement comprising:

a flexible guidewire member formed of metal wire and having a proximal end which remains outside of the patent's body and a distal end for introduction into the vascular system of the patient, the flexible guidewire having a magnetically-attractable element along the length of the guidewire member in a location that is spaced a substantial distance from said distal end so that the magnetically-attractable element is adapted to remain outside of the patient's body.

2. The guidewire member of claim 1, in which said magnetically-attractable element comprises a ferromagnetic portion.

3. The guidewire member of claim 2, in which said ferromagnetic portion comprises a plurality of spaced ferromagnetic segments.

4. The guidewire member of claim 2, in which said ferromagnetic portion extends for at least 15 cm along said guidewire member.

5. The guidewire member of claim 2, in which said ferromagnetic portion is located adjacent the proximal end of the guidewire member.

6. For use in catheter exchange in the vascular system of a patient in which a catheter is advanced over a guidewire member and thereafter the catheter is withdrawn over the guidewire member while the guidewire member is retained in position in the vascular system of the patient, the improvement comprising:

a flexible guidewire member having a proximal end which remains outside of the patent's body and a distal end for introduction into the vascular system of the patient, the flexible guidewire having a magnetically-attractable element along the length of the guidewire member in a location that is spaced a substantial distance from said distal end so that the magnetically-attractable element is adapted to remain outside of the patient's body;

said magnetically-attractable element comprising a plurality of spaced ferromagnetic segments and a plurality of permanent magnets interposed between the spaced ferromagnetic segments.

7. For use in an apparatus for facilitating catheter exchange in the vascular system of a patient, in which a flexible guidewire member formed of metal wire is introduced into the vascular system of the patient, a catheter is advanced over the guidewire member, and thereafter the catheter is withdrawn over the guidewire member while the guidewire member is retained in position in the vascular system of the patient, the improvement comprising:

a device having a magnet adapted for positioning outside of the patient's body in close proximity to a proximal portion of said guidewire member which remains outside of the patient's body and which guidewire member carries a magnetically-attractable element outside of the patient's body, said magnet being adapted for positioning in a magnetic relationship with said magnetically-attractable element to retain said guidewire member in position via magnetic force.

8. A device as defined by claim 7, in which said magnet is a permanent magnet.

9. For use in an apparatus for facilitating catheter exchange in the vascular system of a patient, in which a flexible guidewire member is introduced into the vascular system of the patient, a catheter is advanced over the guidewire member, and thereafter the catheter is withdrawn over the guidewire member while the guidewire member is retained in position in the vascular system of the patient, the improvement comprising:

a device having a magnet adapted for positioning outside of the patient's body in close proximity to a proximal portion of said guidewire member which remains outside of the patient's body and which guidewire member carries a magnetically-attractable element outside of the patient's body, said magnet being adapted for positioning in a magnetic relationship with said magnetically-attractable element to retain said guidewire member in position via magnetic force;

said magnet is an electromagnet.

* * * * *

UNITED STATES PATENT AND TRADEMARK OFFICE
CERTIFICATE OF CORRECTION

PATENT NO. : 5,542,938
DATED : August 6, 1996
INVENTOR(S) : Ernesto Avellanet, Ernesto Hernandez It is certified that error appears in the above-indentified patent and that said Letters Patent is hereby corrected as shown below:

Title page, left column,"[*] Notice" section delete "The term of this patent shall not extend beyond the expiration date of Pat. No. 5,269,758." and substitute --The term of this patent shall not extend beyond the expiration date of Pat. No. 5,269,759.-- therefor.

Signed and Sealed this

Twenty-sixth Day of November 1996

BRUCE LEHMAN

*Attest:*

*Attesting Officer*  *Commissioner of Patents and Trademarks*